United States Patent

Karpowycz

[11] Patent Number: 4,479,057
[45] Date of Patent: Oct. 23, 1984

[54] AUTOMATIC BIASING CONTROL CIRCUIT FOR EMISSIONS DETECTOR

[75] Inventor: Ihor B. Karpowycz, Chicago, Ill.

[73] Assignee: Sun Electric Corporation, Crystal Lake, Ill.

[21] Appl. No.: 424,082

[22] Filed: Sep. 27, 1982

[51] Int. Cl.³ .............................................. G01N 21/35
[52] U.S. Cl. ..................................................... 250/343
[58] Field of Search ......................................... 250/343

[56] References Cited

U.S. PATENT DOCUMENTS 3,678,269 7/1972 Malek ................................. 250/341
4,394,575 7/1983 Nelson ............................... 250/343

Primary Examiner—Janice A. Howell
Assistant Examiner—Constantine Hannaher
Attorney, Agent, or Firm—Allegretti, Newitt, Witcoff & McAndrews

[57] ABSTRACT

A pair of operational amplifiers, one of which having a photoresistor feedback connecting the output of the amplifier to its inverting input. The non-inverting input of the last named amplifier being provided with a voltage developed by the second operational amplifier. The second amplifier serves to control the output of the first amplifier in accordance with changes in the output.

7 Claims, 1 Drawing Figure

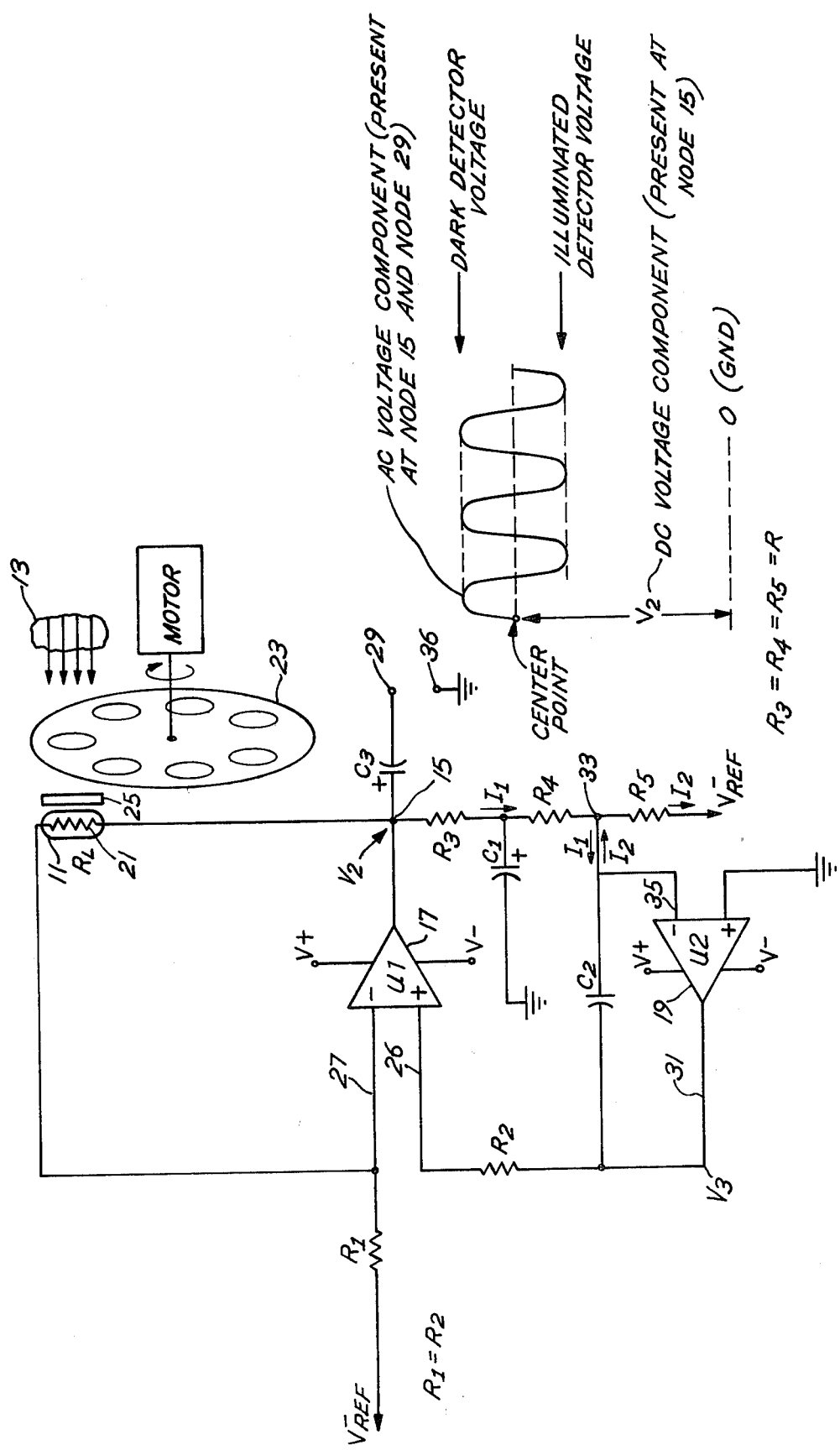

AUTOMATIC BIASING CONTROL CIRCUIT FOR EMISSIONS DETECTOR

BACKGROUND OF THE INVENTION

The invention relates to circuitry for an emissions analyzer which analyzes the exhaust gas stream of an internal combustion engine, and more particularly to an automatic biasing control circuit for an infrared detector utilized in an emissions analyzer.

The circuitry embodiment of the invention described herein is used in an emissions analyzer which analyzes the exhaust gas stream of an internal combustion engine. Specifically, the described circuitry optimizes the constant current bias on an infrared detector. Heretofore, the practice has been to bias the infrared detector of an analyzer either from a constant voltage source such as ±15 VDC, with the detector in series with a fixed resistor, or from a constant current source, in which case a trimpot current adjustment is required due to wide variations in the resistance of commercially available detectors.

The present invention circumvents these requirements by adjusting the detector current automatically without the need for manual trimpot adjustments.

It is therefore an object of the present invention to provide an improved circuit for biasing the emissions detector of an exhaust gas analyzer.

It is a further object of the present invention to provide an automatic biasing control circuit for a radiant energy detector.

SUMMARY OF THE INVENTION

These and other objects of the invention are achieved in circuitry which monitors the signal output of a radiant energy detector. An electrical signal is developed in accordance with the output and is utilized to control the drive signal of the radiant energy detector.

BRIEF DESCRIPTION OF THE DRAWING

The single drawing is an electrical schematic diagram and voltage waveform representation, of a preferred embodiment of the invention.

DETAILED DESCRIPTION OF THE PREFERRED EMBODIMENT

Referring to the single figure, a radiant energy detector 11 is responsive to radiant energy (indicated by reference numeral 13) for developing an output signal at a circuit node 15. The voltage amplitude of the output signal at node 15 is proportional in magnitude to the quantity of radiant energy detected by detector 11. A pair of operational amplifiers 17, 19 is connected in a particular circuitry configuration in order to maintain a relatively fixed voltage center point about which swings the voltage output signal developed at node 15.

Detector 11 includes a photoresistor 21 having a resistance $R_L$ which varies in accordance with the amount of light impinging the detector. The photoresistor may be a lead selenide detector or a lead sulfide detector, or another type of radiant energy detector as will suggest itself.

As understood, the voltage across the photodetector is equal to current through the detector times its resistance: $V = I_L (R_L)$. Where the current $I_L$ is held constant, then the voltage across the photoresistor varies in accordance with variation in resistance of the photoresistor.

The embodiment shown in the single figure may be used to analyze exhaust gas emissions from an automotive engine. The radiant energy 13 is chopped by a rotating chopper wheel 23. A filter 25 is positioned between the chopper wheel and the photoresistor for filtering the chopped radiant energy. The filter filters out all but desired wavelengths of radiant energy associated with a particular emissions gas desired to be analyzed, e.g., carbon dioxide, carbon monoxide, hydrocarbons, etc. The wavelength is associated with the gas absorption characteristic of the particular emissions gas. Thus, the voltage appearing at node 15 will be an A.C. signal component on top of a D.C. voltage component.

As illustrated in the graph to the right of node 15, a voltage $V_2$ is illustrated as the "center point" of the voltage amplitude of the voltage signal at node 15. When there is no light impinging detector 11, the detector resistance $R_L$ increases to its dark resistance value, causing the voltage level at node 15 to rise to the "dark detector voltage" as indicated in the figure. When detector 11 is fully illuminated, the detector resistance $R_L$ decreases to its illuminated resistance value, causing the voltage level at node 15 to decrease to the "illuminated detector voltage". As the particular amount of radiant energy is chopped and then detected by detector 11, a resulting voltage output oscillates between the dark detector voltage and the illuminated detector voltage.

Operational amplifier 17 includes a non-inverting input 26, an inverting input 27 and an output node 15. Capacitor C3 serves to separate the D.C. voltage component $V_2$ from the A.C. signal voltage component. Photoresistor 21 is connected in the feedback path between output node 15 and inverting input 27. Inverting input 27 is connected to a reference voltage $V_{ref}$ via a resistor R1. $V_{ref}$ is a negative voltage having a magnitude substantially equal to one half $V_2$. That is, $V_2 = 2 V_{ref}$. Operational amplifier 17 serves to generate a constant current through detector 11.

The magnitude of the current generated by operational amplifier 17 through photoresistor 21 depends on the magnitude of the voltage differential appearing between the inverting input 27 and the output 15. This voltage is controlled by operational amplifier 19. Operational amplifier 19 has its output 31 connected to the non-inverting input 26 of amplifier 17, via a fixed resistance R2. Operational amplifier 19 develops a voltage $V_3$ at its output 31, of a specific magnitude with respect to $V_{ref}$. The difference in voltage between $V_{ref}$ and V3 when multiplied by the resistance ratio $R_L/R1$ and that product then added to V3 will result in an output voltage V2 at node 15, according to the equation:

$$V_2 = (V_3 - V_{ref}) R_L / R1 + V_3$$

The resulting voltage $V_2$, having a magnitude twice that of $V_{ref}$, causes a current $I_1$ to flow through resistors R3 and R4. $V_{ref}$ also causes a current $I_2$ to flow through resistor R5. Since resistors R3, R4 and R5 are of equal value, currents $I_1$ and $I_2$ are substantially D.C. currents of equal magnitudes and opposing polarity. The A.C. signal component resulting from the chopping of the light is substantially bypassed by a capacitor C1 which connects the node between resistors R3 and R4 to ground. Further, a capacitor C2 connects the inverting input of operational amplifier 19 to its output for forming an integration function. Thus, any A.C. signal component remaining despite capacitor C1 is integrated by operational amplifier 19 to substantially eliminate the A.C. component appearing at node 31.

For the circuit to function properly, a steady state condition has to be reached requiring a very small imbalance in $I_1$ and $I_2$ currents. Since $I_2$ is generated by a stable reference voltage $V_{ref}$, it will always be constant. The $I_1$ current will have a certain imbalance element $I_n$, of positive or negative magnitude.

When $V_2$ becomes greater than $2 V_{ref}$ the $I_n$ will be positive in value. When $V_2$ becomes smaller than $2 V_{ref}$ the $I_n$ will be negative in value. Without this imbalance current $I_n$, the $V_3$ output voltage of operational amplifier 17 would always be zero. This $I_n$ is the error current which establishes an error voltage V3 at output 31 of operational amplifier 19, which in turn corrects the output voltage $V_2$ to a steady state condition. This steady state condition will exist as long as the voltage $V_2$ remains constant. Any change in $V_2$ will cause an imbalance in the circuit loop. If by some chance the $V_2$ increases by certain small amount, this change will cause an increase in current $I_n$, in turn the $I_n$ will cause $V_3$ to become more negative, which will decrease the voltage differential between $V_{ref}$ and $V_3$ which will cause $V_2$ to decrease to lesser magnitude, and thus reestablish again a steady state condition.

It is to be understood, of course, that the foregoing describes a preferred embodiment of the present invention and that modifications may be made therein without departing from the spirit or scope of the present invention as set forth in the appended claims.

What is claimed is:

1. For use in an automotive exhaust emissions analyzer, an automatic bias control circuit for a radiant energy detector, comprising:

radiant energy detector means responsive to radiant energy for generating a signal output having a first signal characteristic varying in time in accordance with the amount of radiant energy detected by said radiant energy detector means, said detector means being driven by an electrical signal having a second signal characteristic;

signal source means for connection to said radiant energy detector means for generating said electrical signal having said second signal characteristic, said signal source means monitoring a developed signal for adjusting the magnitude of said second signal characteristic; and automatic adjustment means for monitoring said first signal characteristic for generating said developed signal.

2. An automatic bias control circuit according to claim 1 wherein said radiant energy detector means is a photoresistor.

3. An automatic bias control circuit according to claim 2 wherein said second signal characteristic is current.

4. An automatic bias control circuit according to claim 3 wherein said signal source means includes an operational amplifier for generating said electrical signal.

5. An automatic bias control circuit according to claim 4 wherein said photoresistor is connected in a feedback path between the output and input of said operational amplifier.

6. An automatic bias control circuit according to claim 4 wherein said operational amplifier has an inverting input and a non-inverting input, one of said inputs being connected to a fixed reference voltage and the other of said inputs being connected to said developed signal.

7. An automatic bias control circuit according to claim 6 wherein said automatic adjustment means includes another operational amplifier for generating said developed signal.

* * * * *